United States Patent [19]

Palfreyman et al.

[11] 4,346,110
[45] Aug. 24, 1982

[54] METHOD FOR TREATING DEPRESSION

[75] Inventors: Michael G. Palfreyman, Fegersheim; Ian A. McDonald, Truchtersheim, both of France

[73] Assignee: Merrell Toraude et Compagnie, Strasbourg, France

[21] Appl. No.: 268,554

[22] Filed: Jun. 1, 1981

[51] Int. Cl.$^3$ .................... A61K 31/24; A61K 31/195
[52] U.S. Cl. ..................................... 424/319; 424/309
[58] Field of Search ............................... 424/309, 319

[56] References Cited

PUBLICATIONS

R. Chari, Ph.D Dissertation, University of Detroit, (1979), "Synthesis of $\beta,\gamma$-Unsaturated Amino Acids as Potential Irreversible Enzyme Inhibitors".

R. Chari et al., *Tetrahedron Letters*, No. 2, pp. 111–114, (1979).

*Primary Examiner*—Stanley J. Friedman
*Attorney, Agent, or Firm*—David E. Frankhouser; Raymond A. McDonald; Gary D. Street

[57] ABSTRACT

2-Amino-3-(3'-hydroxyphenyl)-3-butenoic acid or 2-amino-3-(3',4'-dihydroxyphenyl)-3-butenoic acid can be used to treat depression either alone or in combination with an extracerebrally acting AADC inhibitor.

3 Claims, No Drawings

METHOD FOR TREATING DEPRESSION

This invention relates to a novel method for treating depression.

The class of compounds known as monoamine oxidase inhibitors (MAO inhibitors) has been employed in psychiatry for over 20 years for the treatment of depression, [See Goodman and Gilman, *The Pharmacological Basis of Therapeutics,* 6th Ed, McMillan Publishing Co., Inc., N.Y., 1980, pages 427–430]. MAO inhibitors currently used in the USA for treating depression are tranylcypromine (PARNATE, SKF), phenelzine (NARDIL, Parke-Davis), and isocarboxazid (MARPLAN, Roche). In addition, another MAO inhibitor, pargyline (EUTRON, Abbott), is available for the treatment of hypertension [See *Physicians' Desk Reference,* 34th Ed., Medical Economics Co., Oradell, N.J., 1980, pages 1327–1328 (phenelzine), pages 1466–1468 (isocarboxazid), pages 1628–1630 (tranylcypromine) and pages 521–522 (pargyline)]. MAO inhibitors can also be employed to treat other psychiatric disorders, such as phobic anxiety states.

It is believed that the MAO inhibitors act to alleviate psychiatric disorders, such as depression, by increasing the concentration of one or more biogenic monoamines in the central nervous system. The monoamine oxidase enzyme (MAO) plays an important role in the metabolic regulation of the monoamines since it catalyzes the biodegradtion of the monoamines through oxidative deamination. By inhibiting MAO, the degradation of the monoamines is blocked, and the result is an increase in the availability of the monoamines for their physiological functions. Among the physiologically active monoamines which are known substrates for MAO are: (a) the so-called "neurotransmitter" monoamines, such as the catecholamines (e.g. dopamine, epinephrine, and norepinephrine) and the indoleamines (e.g. tryptamine and 5-hydroxytryptamine), (b) the so-called "trace" amines (e.g. o-tyramine, phenethylamine, tele-N-methylhistamine), and (c) tyramine.

The usefulness of the MAO inhibitors in treating depression has been limited because the administration of such agents can potentiate the pharmacological actions of certain food substances or drugs leading to dangerous and sometimes lethal effects. For example, persons receiving an MAO inhibitor must avoid the ingestion of foods which have a high tyramine content (such as cheese) because the MAO inhibitor will block the metabolic degradation of tyramine in the gut and liver resulting in high circulating levels of tyramine, consequent release of catecholamines in the periphery, and finally serious hypertension. The potentiation by a MAO inhibitor of the pressor effect of tyramine arising from the ingestion of cheese, and the hypertensive episode produced thereby, are commonly known as the "cheese reaction" or "cheese effect". Moreover, persons on conventional MAO therapy can not be given directly-acting sympathomimetic drugs (or precursors thereof) which are themselves substrates for MAO (e.g. dopamine, epinephrine, norepinephrine, or L-DOPA) and of indirectly-acting sympathomimetic drugs (e.g. amphetamines or over-the-counter cold, hay-fever, or weight control preparations which contain a vasoconstrictor). The potentiation of the pressor effects of indirectly-acting sympathomimetic drugs is especially profound. This is because such drugs act peripherally primarily by releasing catecholamines in nerve endings, and the concentration of the liberated catecholamines will be dangerously elevated if the metabolic degradation of the catecholamines via MAO is blocked. In addition, a particular MAO inhibitor should not be used in combination with another MAO inhibitor or with hypotensive agents, dibenzapine antidepressants, meperidine, CNS depressants, and anticholinergic agents.

Biochemical and pharmacological studies indicate that the MAO enzyme exists in two forms known as "MAO Type A" (MAO-A) and "MAO Type B" (MAO-B). The forms differ in their distribution in body organs, in their substrate specificity, and in their sensitivity to inhibitors. In general, MAO-A selectively oxidizes the so-called "neurotransmitter" monoamines (epinephrine, norepinephrine, and 5-hydroxytryptamine) while MAO-B selectively oxidizes the "trace" monoamines (o-tyramine, phenethylamine, and tele-N-methylhistamine). Both MAO-A and MAO-B oxidize tyramine, tryptamine, and dopamine. However, in man, dopamine has been shown to be a preferred substrate for MAO-B. The forms also differ in their sensitivity to inhibition, and thus, can be preferably inhibited depending upon the chemical structure of the inhibitor and/or the relative concentrations of the inhibitor and the enzyme. The MAO inhibitors currently sold in the U.S. for the therapy of depression (tranylcypromine, phenelzine, and isocarboxazid) are not preferential in their action upon MAO. However, various chemical compounds are known in the art to be preferential inhibitors of MAO, the most important being clorgyline, pargyline, and L-deprenyl which are all reported to be clinically effective antidepressant agents. MAO-A is preferentially inhibited by clorgyline, while MAO-B is preferentially inhibited by pargyline and L-deprenyl. It should be observed that the "selectivity" of an MAO inhibitor arises because the inhibitor has a greater affinity for one form of the enzyme. Thus, the selectivity of an MAO inhibitor for MAO-A or MAO-B in vivo will be dose-dependent, selectivity being lost as the dosage is increased. Clorgyline, pargyline, and L-deprenyl are selective inhibitors at lower dosages, but are not selective inhibitors at higher dosages. The literature concerning MAO-A and MAO-B, and the selective inhibition thereof, is extensive [See, for example, Goodman and Gilman, ibid, pages 204–205; Neff et al, *Life Sciences,* 14, 2061 (1974); Murphy, *Biochemical Pharmacology,* 27, 1889 (1978); Knoll, Chapter 10, pages 151–171 and Sandler, Chapter 11, pages 173–181, in *Enzyme Inhibitors as Drugs,* M. Sandler, Ed., Macmillan Press Ltd., London, 1980; Lipper et al, *Psychopharmacology,* 62, 123 (1979); Mann et al, *Life Sciences,* 26, 877 (1980); and various articles in *Monoamines Oxidase: Structure, Function, and Altered Functions,* T. Singer et al, Ed., Academic Press, N.Y 1979].

Of the selective inhibitors of MAO, L-deprenyl is of interest since the "cheese effect" is not observed at the low dosages where preferential inhibitions of MAO-B occur. [See Knoll, *TINS,* pages 111–113, May 1979]. This observation is not unexpected since the intestinal mucosa contains predominantely MAO-A which, because it is not inhibited, permits oxidation and removal of the ingested tyramine. The selectivity of L-deprenyl for MAO-B may account for its ability to potentiate L-DOPA for the treatment of Parkinson's disease without producing peripheral side effects, such as hypertension due to potentiation of pressor catecholamines [See Lees et al, *Lancet,* pages 791–795, Oct. 15, 1977 and Birkmeyer, *Lancet,* pages 439–443, Feb. 26, 1977].

In its first aspect, the invention sought to be patented comprehends a method for treating depression which comprises administering to a depressed patient an effective amount of 2-amino-3-(3'-hydroxyphenyl)-3-butenoic acid (I) or 2-amino-3-(3',4'-dihydroxyphenyl)-3-butenoic acid (II), or a $C_1$–$C_8$ alkyl ester thereof, or a pharmaceutically acceptable salt thereof.

In its second aspect, the invention comprehends a method for treating depression which comprises administering to a depressed patient an effective amount of 2-amino-3-(3'-hydroxyphenyl)-3-butenoic acid (I) or 2-amino-3-(3',4'-dihydroxyphenyl)-3-butenoic acid (II), or a $C_1$–$C_8$ alkyl ester thereof, or a pharmaceutically acceptable salt thereof, in combination with an effective amount of an AADC inhibitor, the amount of AADC inhibitor being sufficient to substantially block the AADC catalyzed decarboxylation of said compound extracerebrally without substantially blocking the AADC catalyzed decarboxylation of said compound in the brain.

As used herein, "AADC" means the enzyme known as "aromatic L-amino acid decarboxylase".

The structural formulae of 2-amino-3-(3'-hydroxyphenyl)-3-butenoic acid and 2-amino-3-(3',4'-dihydroxyphenyl)-3-butenoic acid are shown below in Formula I and II, respectively:

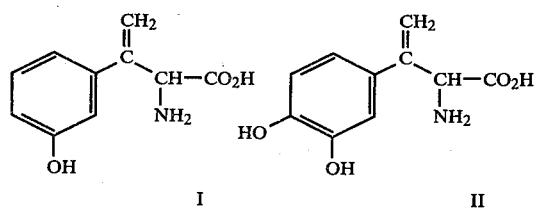

The $C_1$–$C_8$ alkyl esters and the pharmaceutically acceptable salts of compounds I and II can be made by conventional methods.

Suitable non-toxic, pharmaceutically acceptable salts are known in the art and include acid addition salts formed by protonation of the α-amino group and salts formed by neutralization of the carboxylic acid function. As with any amino acid, the compounds may exist in the form of a zwitterion. Examples of acid addition salts are those formed from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic. Examples of salts formed by neutralization of the carboxylic acid are metallic salts (e.g. sodium, potassium, lithium, calcium, or magnesium) and ammonium or (substituted) ammonium salts. The potassium and sodium salts are preferred.

Compounds I and II are metabolic precursors (or "prodrugs") of substances which are irreversible inhibitors of MAO, and said compounds are useful in psychiatry for the treatment of depression. Compounds I and II are not irreversible inhibitors of MAO in vitro. In order to produce irreversible inhibition of MAO in vivo, and to exert their antidepressant effect, compounds I and II must be transformed into active metabolites which are the 2-phenylallylamine compounds shown below respectively in Formula III and IV:

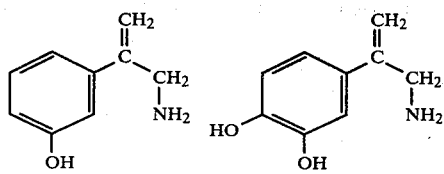

The in vivo transformation of compund I or II to the active metabolites of Formula III or IV occurs through a decarboxylation reaction catalyzed by an enzyme known as "aromatic-L-amino acid decarboxylase" (AADC). AADC is known to decarboxylate various biologically important amino acids (such as dopa, tyrosine, phenylalanine, tryptophan, and 5-hydroxytryptophan) to form the corresponding monoamines.

The antidepressant compounds of Formula III or IV, which inhibit MAO in vitro and in vivo, are described and claimed in the copending application of P. Bey entitled "Allylamine MAO Inhibitors" filed even date herewith, Ser. No. 268,555.

It is known that AADC is present both in the brain and extracerebral tissue. Thus, the decarboxylation of compound I or II can take place both in the brain and in extracerebral tissue with consequent inhibition of MAO. By administering compound I or II in combination with a compound capable of preferentially blocking extracerebral AADC, the decarboxylation reaction producing the active metabolite will take place primarily in the brain, and hence primarily the brain MAO will be inhibited. The administration of compound I or II in combination with a peripheral AADC inhibitor for the treatment of depression, therefore, offers the advantages of substantially avoiding the "cheese effect" and other peripheral complications that are commonly associated with conventional MAO inhibitor therapy. In combination with an extracerebral AADC inhibitor, compound I or II will provide a "site-directed" inhibition of MAO, the inhibition being confined primarily to the brain which has high AADC activity.

Suitable AADC inhibitors for use in combination with compounds I and II will be apparent to those skilled in the art. Both competitive and irreversible inhibitors can be used. At the dosages used, the AADC inhibitor must be capable of inhibiting AADC extracerebrally without substantially inhibiting AADC in the brain. Examples of AADC inhibitors for use in combination with compounds I and II are carbidopa and benserazide, compounds which also have been found useful for blocking the peripheral decarboxylation of exogenous L-dopa administered for the treatment of Parkinsonism [See Chapter 21, especially pages 482 and 483, "The Pharmacological Basis of Therapeutics", Goodman and Gilman, Ed., Macmillan Publishing Co., Inc., N.Y., 6th Ed., 1980]. Other examples of suitable AADC inhibitors are the 2-amino-2-(monofluoromethyl or difluoromethyl)-3-(monohydroxyphenyl or dihydroxyphenyl)propionic acids, and like compounds, which are described and claimed in the copending patent application of P. Bey and M. Jung entitled "α-Halomethyl Amino Acids", Ser. No. 210,500 filed Nov. 26, 1980, the full disclosure of which is specifically incorporated herein by reference. The aforesaid 2-halomethylated 2-amino-3-(substituted phenyl)propionic acids are also described in Belgian Pat. Nos.

868,881 and 822,105. Preferred compounds are 2-amino-2-(monofluoromethyl or difluoromethyl)-3-(3',4'-dihydroxyphenyl)propionic acids, or a 2',3' or 2',5'-dihydroxyphenyl isomer thereof.

The preparation of 2-amino-3-(3'-hydroxyphenyl)-3-butenoic acid (I) from methyl 3-(3'-tetrahydropyranyloxyphenyl)-2-butenoate is described by R. Chari in the Doctoral Dissertation entitled "Synthesis of β,γ-Unsaturated Amino Acids as Potential Irreversible Inhibitors", University of Detroit, 1979 (available in print from University Microfilm International, Ann Arbor, Mich.).

In the method of Chari, methyl 3-(3'-tetrahydropyranyloxyphenyl)-2-butenoate is brominated in carbon tetrachloride at −10° C. to form the corresponding dibromo compound which upon treatment with ammonia in dimethyl sulfoxide (DMSO) affords methyl 2-amino-3-(3'-tetrahydropyranyloxyphenyl)-3-butenoate. This intermediate can be converted to compound I in two stages: (a) treatment with saturated ethereal hydrogen chloride at ambient temperature, under which conditions the aromatic —OH protecting group is removed, and (b) treatment with 6 N hydrochloric acid at reflux temperature under which conditions the ester group is hydrolyzed.

A modification of the above-described method involves the preparation and isolation of ethyl 2-(tert-butoxycarbonylamino)-3-(3'-tetrahydropyranyloxyphenyl)-3-butenoate. This intermediate is prepared by treating methyl 2-amino-3-(3'-tetrahydropyranyloxyphenyl)-3-butenoate, as prepared according to the above-described method of Chari, with 2-(tert-butoxycarbonyloxyimino)-2-phenylacetonitrile in tetrahydrofuran at 60° C. for about 2-4 hours. The intermediate can be converted to compound I by a three-stage procedure which comprises: (a) treating the N-tert-Boc derivative with lithium hydroxide in dimethoxyethane/water at ambient temperature to hydrolyze the ester function, (b) neutralizing the lithium salt then formed with dilute hydrochloric acid (to pH ca 4.0) to form the corresponding free acid, and (c) treating the free acid with saturated ethereal hydrogen chloride at 0° to 25° C. for about 16 hours to remove both the aromatic —OH protecting group and the tert-Boc group.

The modified procedure for preparing 2-amino-3-(3'-hydroxyphenyl)-3-butenoic acid is described in Example II herein. 2-Amino-3-(3',4'-dihydroxyphenyl)-3-butenoic acid (II) can be prepared from ethyl 3-(3',4'-di-tert-butyldimethylsilyloxyphenyl)-2-butenoate by following the procedures of Example II, Steps A, B, and C, to prepare 2-(tert-butoxycarbonylamino)-3-(3',4'-di-tert-butyldimethylsilyloxyphenyl)-3-butenoic acid. The tert-butyldimethylsilyl protecting groups are then removed by treating the intermediate with tetra-n-butylammonium fluoride in tetrahydrofuran at ambient temperature. 2-Amino-3-(3',4'-dihydroxyphenyl)-3-butenoic acid, as the hydrochloride salt, can be obtained by removing the tert-Boc protecting group using saturated hydrogen chloride in ether, as described in Example II, Step D. The free amino acid can be obtained, if desired, by treatment with propylene oxide according to the procedure described in Example II, Step E.

The tert-butyldimethylsilyl protecting group should be used to protect the aromatic hydroxy groups in the preparation of 2-amino-3-(3',4'-dihydroxphenyl)-3-butenoic acid since it can be removed under very mild conditions. The use of lithium hydroxide to hydrolyze the ester function and mild conditions to remove the protecting groups will minimize the occurence of side reactions involving the double bond (e.g. polymerization) which reactions are promoted under vigorous acidic conditions. Use of the N-tert-Boc intermediate rather than the free amine intermediate avoids decomposition of the amino acid during the subsequent base hydrolysis step and aids in purification of the hydrolysis product.

The starting materials for the bromination reaction (methyl or ethyl 3-(3'-tetrahydropyranyloxyphenyl)-2-butenoate and ethyl 3-(3',4'-di-tert-butyldimethylsilyloxyphenyl)-2-butenoate) can be prepared in known manner by the Wittig reaction by treating the appropriate OH-protected ketone with a suitable trialkylphosphonoacetate in DME at 0° C. in the presence of sodium hydride. The ketones are known compounds. Examples I herein illustrates the preparations of ethyl 3-(3'tetrahydropyranyloxyphenyl)-2-butenoate from 3-tetrahydropyranyloxyacetophenone.

As will be appreciated by those skilled in the art, compounds I and II have an aromatic —OH group and an alpha-$NH_2$ group, one or both of which may be acylated in known manner. It is known in the art that the N-acyl or O-acyl groups derived from $C_1$-$C_4$ alkanoic acid (e.g. acetyl) or a naturally occurring amino acid (i.e. L-glycyl or L-alanyl) can be metabolically removed to generate the free —$NH_2$ group or —OH group in vivo. Thus the acyl derivatives can also be employed for the purposes of this invention, provided that the acyl group cn be removed in vivo to give the desired amino acid. It will also be apparent that certain derivatives of the carboxylic acid function, other than esters and salts, can be employed for the purposes of this invention. Examples are primary amides, secondary or tertiary alkyl amides, and amides formed from the alpha- or terminal $NH_2$— group of natural amino acids, since it is known in the art that the amide bond can be cleaved metabolically.

Since compounds I and II possess an asymmetric carbon atom, enantiomers are possible, and the compounds of the invention may be in the form of the biologically active enantiomer or the racemate. The compounds may be obtained in the form of a pure enantiomer either by resolving a desired racemic product or by resolving a racemic starting material or intermediate at any convenient stage of the synthesis. Methods of carrying out the resolution are well known in the art of chemistry. When dosage ranges are given herein, they are applicable to the racemate.

When employed to treat depression, the effective dosage of compound I or II will vary according to the particular compound being employed, the severity and nature of the depression, and the particular subject being treated. In general, effective results can be achieved by the oral or parenteral route at a dosage level of from about 20 to 200 mg per day. Therapy shuld be initiated at lower dosages, the dosage thereafter being increased until the desired effect is achieved.

When an AADC inhibitor is co-administered with compound I or II for the treatment of depression, the effective dosage of the AADC inhibitor must be capable of substantially blocking the AADC catalyzed decarboxylation of said compound extracerebrally without substancially blocking the AADC catalyzed decarboxylation in the brain. The effective dose will vary however, according to the particular compound being employed and the dose of the antidepressant "prodrug" administered. In general, with carbidopa and benzerazide effective results can be achieved by the oral or parenteral route at a dosage level of about 50 to 500 mg per day, preferably about 50 to 250 mg. With the 2-halomethylated 2-amino-3-(substituted phenyl)propionic acids described supra, effective results can be achieved by the oral or parenteral route at a dosage level of about 0.1 mg to 1000 mg per day. For example, with 2-amino-2-difluoromethyl-3-(3',4'-dihydroxyphenyl)propionic acid, and like compounds, the effective dose is about 10 to 1000 mg. per day, preferably about 100 to 500 mg. With 2-amino-2-fluoromethyl-3-(3',4'-dihydroxyphenyl)propionic acid, and like compounds, such as the 2,3-dihydroxyphenyl isomer thereof, the effective dose is about 0.1 to 50 mg per day, preferably about 0.5 to 10 mg.

It will be understood that the AADC inhibitor can be co-administered either substantially at the same time as or prior to the administration of compound I or II. When administered prior, the AADC inhibitor can be given up to 4 hours prior, depending upon the route of administration and severity of the conditions being treated.

When used in combination with an AADC inhibitor, compound I or II and the AADC inhibitor can be administered separately, each being contained in the formulation in which the compound or the AADC inhibitor is the sole active agent, or they can be administered together in a formulation containing both the compound and the AADC inhibitor as active agents. When both agents are contained in a single formulation, the relative amounts of each agent can vary depending upon the particular compound employed.

When employed for the treatment of depression, the active substances may be administered alone or in combination with pharmaceutically acceptable carriers, the proportion and nature of which are determined by the solubility and chemical properties of the compound selected, the chosen route of administration, and standard pharmaceutical practice. For example, the agents may be administered orally in solid dosages forms, e.g. capsules, tablets, or powders, or in liquid forms, e.g. solutions or suspensions. The agents may also be injected parenterally in the form of sterile solutions or suspensions. Solid oral forms may contain conventional excipients, for instance: lactose, sucrose, magnesium stearate, resins, and like materials. Liquid oral forms may contain various flavoring, coloring, preserving, stabilizing, solubilizing or suspending agents. Parenteral preparations are sterile aqueous or nonaqueus solutions or suspensions which may contain various preserving, stabilizing buffering, solubilizing, or suspending agents. If desired, additives, such as saline or glucose may be added to make the solutions isotonic.

The following examples are illustrative of the processes of the invention. All temperatures are in centigrade.

EXAMPLE I

Ethyl 3-(3'-tetrahydropyranyloxyphenyl)-2-butenoate

A solution of diethyl ethoxycarbonylmethanephosphonate (10.3 g) in dimethoxyethane (100 ml) is added dropwise to a cooled (0°) suspension of sodium hydride (1.2 g) in dimethoxyethane (50 ml). When the addition is complete (about 30 minutes), the cooling-bath is removed and the mixture is stirred for a further 2 hours. To this mixture is slowly added a solution of 3-tetrahydropyranyloxyphenylacetophenone (10.0 g) in dimethoxyethane (200 ml) at room temperature. The reaction mixture is then heated at about 70° for 4 hours, cooled to room temperature, and poured into water (1 l). Ether extraction followed by silica gel (200 g) chromatography (light petroleum (80%)/ether (20%) as eluant) enables the isolation of pure ethyl 3-(3'-tetrahydropyranyloxyphenyl)-2-butenoate (8.45 g): colorless oil; N.M.R. (CDCl$_3$): $\delta$1.27, t(J=7 Hz), 3H; 1.40 to 2.07, m, 6H; 2.50, d(J=1.5 Hz), 3H; 3.33 to 3.93, m, 2H; 4.13, q(J=7 Hz), 2H; 5.35, s(broad), 1H; 4.37, t(J=1.5 Hz), 1H; 6.83 to 7.57, m, 4H.

EXAMPLE II

Step A: Ethyl 2,3-Dibromo-3-(3'-tetrahydropyranyloxyphenyl)butyrate

A solution of bromine (3.50 g) in carbon tetrachloride (60 ml) is added dropwise to a cooled (−10°) solution of ethyl 3-(tetrahydropyranyloxyphenyl)-2-butenoate (5.80 g) and pyridine (10 drops) in carbon tetrachloride (60 ml). After the completion of the addition, the reaction mixture is stirred for 1 hour at about −10°, and the solvent is evaporated to leave an orange oil (9.42 g). Chromatography on silica gel (200 g) using a mixture of light petroleum (80%) and ether (20%) as eluant allows the separation of pure ethyl 2,3-dibromo-3-(3'-tetrahydropyranyloxyphenyl)butyrate (5.47 g): colorless oil; N.M.R. (CDCl$_3$): $\delta$1.37, t(J=7 Hz), 3H; 1.27 to 2.20, m, 6H; 2.55, s, 3H; 3.40 to 4.13, m, 2H; 4.33, q(J=7 Hz), 2H; 5.05, s, 1H; 5.10, s(broad), 1H; 6.73 to7.43, m, 4H.

Step B: (Racemic) Ethyl 2-(tert-Butoxycarbonylamino)-3-(3'-tetrahydropyranyloxyphenyl)-3-butenoate A saturated solution of ammonia in dimethyl sulfoxide (20 ml) is added to ethyl 2,3-dibromo-3-(3'-tetrahydropyranyloxyphenyl)butyrate (1.5 g) in a suitable pressure-vessel at about 5°. The reaction vessel is firmly sealed. The solution is left at ambient temperature for 40 hours and is then poured into ice-cold water (200 ml), which is extracted with dichloromethane. The organic extract is thoroughly washed with water, dried, and evaporated to leave a yellow oil (0.64 g).

A solution of this material and 2-(tert-butoxycarbonyloxyimino)-2-phenylacetonitrile (0.45 g) in tetrahydrofuran (50 ml) is heated at 60° for 2 hours. Evaporation to dryness leaves an orange oil (0.93 g). Purification is achieved by silica gel (30 g) chromatography using light petroleum (90%)/ether (10%) as eluant whereupn there is obtained racemic ethyl 2-(tert-butoxycarbonylamino)-3-(3'-tetrahydropyranyloxyphenyl)-3-butenoate (0.43 g): colorless oil; N.M.R. (CDCl$_3$): $\delta$1.08, t(J=7 Hz), 3H; 1.37, s, 9H; 1.40 to 2.10, m, 6H; 3.30 to 3.90, m, 2H; 4.08, q, (J=7 Hz), 2H; 4.92 to 5.53, m, 5H: 6.77 to 7.33, m, 4H.

Step C: (Racemic) 2-(tert-Butoxycarbonylamino)-3-(3'-tetrahydropyranyloxyphenyl)-3-butenoic acid A solution of ethyl 2-(tert-butoxycarbonylamino)-3-(3'-tetrahydropyranyloxyphenyl)-3-butenoate (0.40 g) in dimethoxyethane (10 ml) and water (2 ml) is treated with solid lithium hydroxide monohydrate (0.02 g). After stirring for 2 hours at room temperature, the mixture is diluted with water and acidified with 0.1 N hydrochloric acid to ca pH 4. Extraction with ether gives essentially pure racemic 2-(tert-butoxycarbonylamino)-

3-(3'-tetrahydropyranyloxyphenyl)-3-butenoic acid (0.25 g): colorless solid.

Step D: Hydrochloride of (racemic) 2-amino-3-(3'-hydroxyphenyl)-3-butenoic acid A solution of 2-(tert-butoxycarbonylamino)-3-(3'-tetrahydropyranyloxyphenyl)-3-butenoic acid (0.25 g) in ether (10 ml) saturated with dry hydrogen chloride is left standing at about 5° for 16 hours during which time colorless crystals precipitate. These are collected and dried to give the hydrochloride of racemic 2-amino-3-(3'-hydroxyphenyl)-3-butenoic acid (0.12 g): colorless needles; m.p. 199°-200°.

Analysis for $C_{10}H_{12}ClNO_3$: Found: C, 52.08; H, 5.24; N, 5.95%; Requires: C, 52.29; H, 5.27; N, 6.10%

Step E: (Racemic) 2-Amino-3-(3'-hydroxyphenyl)-3-butenoic acid

A solution of the hydrochloride of 2-amino-3-(3'-hydroxyphenyl)-3-butenoic acid (0.12 g) in ethanol (2 ml) is treated with a slight excess of propylene oxide. After several hours, the precipitated material is collected and dried to afford pure racemic 2-amino-3-(3'-hydroxyphenyl)-3-butenoic acid: colorless powder; m.p. 204°-205°; N.M.R. (CDCl$_3$): $\delta$4.8, s obscured by CD$_3$OH peak: 5.33, s,1H; 5.47, s, 1H; 6.47 to 7.13, m, 4H.

What is claimed is:

1. A method for treating depression which comprises administering to a depressed patient an antidepressant effective amount of 2-amino-3-(3'-hydroxyphenyl)-3-butenoic acid or 2-amino-3-(3',4'-dihydroxyphenyl)-3-butenoic acid, or a $C_1$-$C_8$ alkyl ester, or a pharmaceutically acceptable salt thereof.

2. A method as defined in claim 1 wherein the compound administered is 2-amino-3-(3'-hydroxyphenyl)-3-butenoic acid.

3. A method as defined in claim 1 wherein the compound administered is 2-amino-3-(3',4'-dihydroxyphenyl)-3-butenoic acid.

* * * * *